United States Patent [19]

McGredy

[11] Patent Number: Plant 5,849

[45] Date of Patent: Jan. 13, 1987

[54] ROSE PLANT NAMED 'MACANGELI'

[76] Inventor: Samuel D. McGredy, 130 B Beach Rd., Castor Bay, Auckland 9, New Zealand

[21] Appl. No.: 708,407

[22] Filed: Mar. 5, 1985

[51] Int. Cl.[4] ..... A01H 5/00

[52] U.S. Cl. ..... Plt./8

[58] Field of Search ..... Plt./8

*Primary Examiner*—James R. Feyrer

*Attorney, Agent, or Firm*—Vincent G. Gioia

EXEMPLARY CLAIM

A new miniature rose variety of glowing white flower coloring.

1 Drawing Figure

1

The present invention relates to a new and distinct variety of rose plant of the miniature rose class, which was originated by my crossing as seed parent the rose known as "Snow Carpet" and as pollen parent the rose known as Moana". The varietal denomination of this new variety is "Macangeli".

Among the novel characteristics possessed by this new variety which distinguish it from its parents and all other varieties of which I am aware are its glowing white decorative flowers of unusually heavy petalage which maintain their color upon aging. Flowers are long lasting on the plant and after cutting. Asexual reproduction by budding of the new variety as performed in Washington County, Oreg., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "158A" is plate 158A of The Royal Horticultural Society Colour Chart.

Parentage: Seedling.

*Seed parent.*—"Snow Carpet".

*Pollen parent.*—"Moana".

Class: Miniature.

The following observations are made of specimens grown outdoors in Washington County, Oreg., during the month of August.

FLOWER

Blooming habit: Near continuous.

A. Bud:

(1) *Size.*—Small, about 1 cm.

(2) *Form.*—Ovoid (informal).

(3) *Color.*—When sepals first divide and petals begin to unfurl — near chrome yellow 158A.

(4) *Sepals.*—Spear shaped, reflexed, ½ cm longer than bud.

2

(5) *Peduncle.*—Length — about 1½ cm. Aspect — straight. Strength — erect from cascading growth. Color — near 137C.

B. Bloom:

(1) *Size.*—Average size when fully expanded — about 3 cm.

(2) *Borne.*—In sprays.

(3) *Form.*—Informal, decorative, smooth petals opening outward becoming a very full bloom, Chrysanthemum-like appearance.

(4) *Petalage.*—Number of petals under normal conditions — about 35 to 40.

(5) *Color.*—After sepals fall, visible bud coloring is near chrome yellow 158A. When fully open, color is near 155D and remains stable and constant through to maturity. However, fully open blooms have central small yellow annular area where point of petal attachment is most visible. General tonality from a distance is pure glowing white.

C. Petals:

(1) *Texture.*—Medium.

(2) *Appearance.*—Inside — velvety, outside — velvety.

(3) *Form.*—Outer petals are rounded with smooth edge, inner petals oblong.

(4) *Arrangement.*—Regularly arranged, imbricated.

(5) *Petaloids in center.*—Medium.

(6) *Persistence.*—Drop off cleanly.

(7) *Fragrance.*—None.

(8) *Lasting quality.*—Very long lasting on plant and as cut flower.

REPRODUCTIVE ORGANS

A. Stamens, filaments and anthers:

(1) *Arrangement.*—Regularly arranged stamens around a high pistil.

(2) *Color.*—Cream yellow.

B. Pollen:

*Color.*—Light yellow.

C. Styles: Thin, uneven length.

D. Stigmas:

*Color.*—Light yellow.

E. Hips: Globular, rarely formed, about 174 cm, orange, seeds do not protrude.

PLANT

A. Form: Spreading.

B. Growth: Uniform branching, medium vigor.

*Height attained.*—About 25 cm.

C. Foliage: Compound 5 to 7 leaflets.

(1) *Size.*—Small ¼ to ¾ cm leaflets.

(2) *Quantity.*—Abundant.

(3) *Color.*—New foliage: Upper side — near to 137C. Under side — near to 137C. Old foliage: Upper side — near 137B. Upper side — near 137B.

(4) *Shape.*—Oval pointed, supported by petiolule.

(5) *Texture.*—Upper side is glossy.

(6) *Edge.*—Serrated.

(7) *Serration.*—Serrulate.

(8) *Leaf stem.*—Color — red tone turning green.

(9) *Stipules.*—Slightly bearded, ¼ cm.

(10) *Resistance to Disease.*—Blackspot — average. Mildew — average. Rust — average.

D. Wood:

(1) *New wood.*—Color — reddish green. Bark — smooth.

(2) *Old wood.*—Color — near 137C. Bark — smooth, with angled. growth with close internodes.

E. Thorns:

(1) *Thorns.*—Quantity (main stalk) — heavy. On laterals from stalk — plentiful. Form — needle, declining. Length — ⅓ cm. Color — cream turning to light brown. Position — ordinary.

(2) *Prickles.*—Profuse.

F. Winter hardiness: Requires ordinary protection in extreme climates.

I claim:

1. A new and distinct variety of rose plant of the miniature rose class, substantially as shown and described, characterized particularly by heavily petaled glowing white flowers that hold color well through the development and aging.

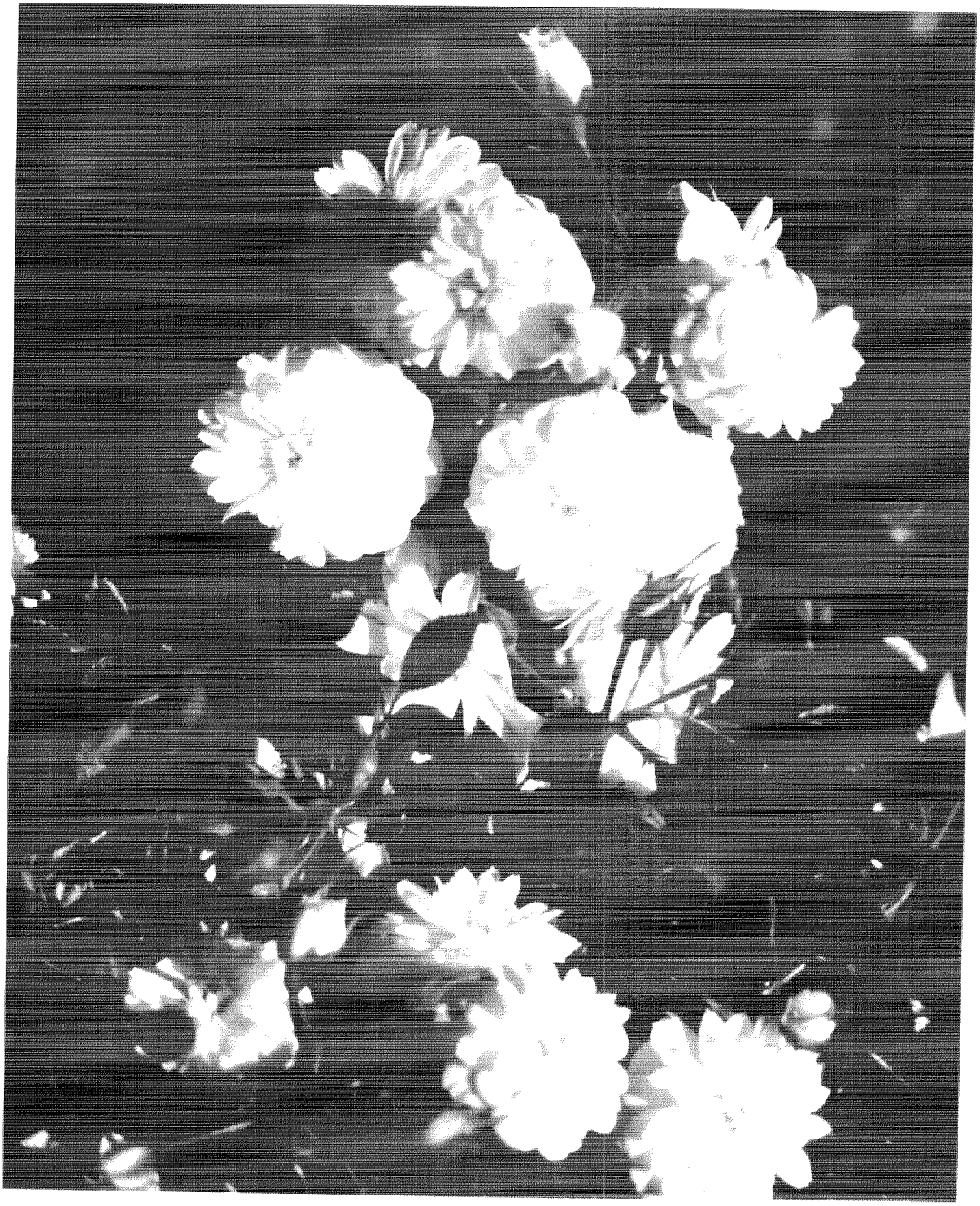

* * * * *